United States Patent
Nunomura et al.

(10) Patent No.: US 7,981,060 B2
(45) Date of Patent: *Jul. 19, 2011

(54) ULTRASOUND APPLYING SKIN CARE DEVICE

(75) Inventors: Mahito Nunomura, Hirakata (JP); Takafumi Oba, Kusatsu (JP)

(73) Assignee: Panasonic Electric Works Co., Ltd., Osaka (JP)

(*) Notice: Subject to any disclaimer, the term of this patent is extended or adjusted under 35 U.S.C. 154(b) by 1622 days.

This patent is subject to a terminal disclaimer.

(21) Appl. No.: 10/560,032

(22) PCT Filed: Jun. 13, 2003

(86) PCT No.: PCT/JP03/07526
§ 371 (c)(1),
(2), (4) Date: Dec. 8, 2005

(87) PCT Pub. No.: WO2004/110558
PCT Pub. Date: Dec. 23, 2004

(65) Prior Publication Data
US 2006/0149169 A1   Jul. 6, 2006

(51) Int. Cl.
*A61H 1/00* (2006.01)
*A61H 1/02* (2006.01)
*A61H 5/00* (2006.01)

(52) U.S. Cl. .......................................... 601/2

(58) Field of Classification Search ....... 601/2; 310/311
See application file for complete search history.

(56) References Cited

U.S. PATENT DOCUMENTS

| 3,553,134 A * | 1/1971 | Ikushima et al. ...... 252/62.9 PZ |
| 6,183,426 B1 | 2/2001 | Akisada et al. |
| 6,576,875 B1 | 6/2003 | Kleffner et al. |
| 2003/0032899 A1* | 2/2003 | Ohba et al. ........................ 601/2 |
| 2004/0171970 A1* | 9/2004 | Schleuniger et al. ............. 601/2 |

FOREIGN PATENT DOCUMENTS

| JP | 7-59197 A | 3/1995 |
| WO | WO-98/51255 | 11/1998 |

OTHER PUBLICATIONS

International Search Report, Feb. 20, 2004.

* cited by examiner

*Primary Examiner* — Tse Chen
*Assistant Examiner* — Jacqueline Cheng
(74) *Attorney, Agent, or Firm* — Cheng Law Group, PLLC (57) ABSTRACT

An ultrasonic skin care device has an applicator head for applying the ultrasound vibrations to a user's skin. The applicator head has a vibrator element and a horn which are integrated into a combined vibration mass that resonates with an electric pulse to produce the ultrasound vibrations. The device is configured to limit the ultrasound upon detection that the applicator head is out of a normal contact with the skin. A load detecting circuit detects whether the applicator head is in a normally loaded condition or in an unloaded condition with reference to electrically equivalent impedance of the combined vibration mass. The combined vibration mass has a structure that restrains vibrations at a center portion of the vibration mass in order to reduce an undesired parasitic resonance, thereby enabling to discriminate the impedance given under the normally loaded condition from that given under the unloaded condition.

13 Claims, 10 Drawing Sheets

ULTRASOUND APPLYING SKIN CARE DEVICE

TECHNICAL FIELD

The present invention is directed to an ultrasound applying skin care device for applying an ultrasound to a user's skin in order to accelerate the metabolism of a skin tissue for making the skin beauty and healthy.

BACKGROUND ART

WO98/51255 discloses a like ultrasound applying skin care device having an applicator head for generating and transmitting an ultrasound to a user's skin. The device includes a load detecting circuit for detection whether the applicator head is loaded by contact with the skin in order to save energy when the applicator head is out of contact with the skin as well as to apply the ultrasound safely when the applicator head is in contact with the skin. For judging whether the applicator head is loaded or unloaded, the device relies on an electrically equivalent impedance of the applicator head which varies with the load acting on the applicator head, and compares a corresponding voltage being applied to the applicator head with a reference voltage. However, when the applicator head gives the ultrasound at a relatively high frequency, for example, several MHz or more, it may be sometimes difficult to discriminate the unloaded condition from the loaded condition on a basis of the electrically equivalent impedance due to an increased effect of a parasitic resonance appearing in the applicator head.

Japanese Patent Publication No. 7-59197 discloses an ultrasonic vibrator element that reduces vibrations occurring around the periphery of the vibrator element. The vibrator element is in the form of a circular disk provided on opposite surfaces thereof respectively with upper and lower circular electrodes. Each of the electrodes has a diameter less than that of the vibrator element to leave the outer periphery of the vibrator element uncovered in an attempt to cancel undesired vibrations propagating in radial directions, thereby allowing intended ultrasonic vibrations to proceed in the thickness direction of the vibrator element.

The parasitic resonance may be reduced with the use of the structure disclosed in the Japanese Patent Publication No. 7-59197 to some extent. After studying the behavior of the ultrasonic vibrations at the high frequency, the inventors have found effective to restrain vibrations occurring at the center of the applicator head in order to reduce undesired parasitic resonance to such an extent that the applicator head can exhibit the electrically equivalent impedances, respectively when being loaded and unloaded, that are sufficiently distinct from each other for easy discrimination between the loaded and unloaded condition.

DISCLOSURE OF THE INVENTION

In view of the above finding, the present invention has been accomplished to provide an ultrasound applying skin care device which is capable of applying the ultrasound effectively and safely for enhancing the skin care.

The skin care device of the present invention includes a housing provided with an applicator head for applying the ultrasound to a user's skin, and a driver circuit that provides an electric pulse for actuating the applicator head to transmit the ultrasound to the skin. The applicator head is composed of a vibrator element generating the ultrasound, and a horn having a mounting face and a skin opposing face for use in contact with the skin. The horn carries the vibrator element on the mounting face to transmit the ultrasound to the skin. The vibrator element and the horn are integrated into a combined vibration mass that resonates with the electric pulse from the driver circuit, thereby transmitting resulting vibrations to the skin. The combined vibration mass gives a first electrically equivalent impedance when it is normally loaded by contact with the skin, and gives a second electrically equivalent impedance when it is unloaded. The device includes a load detecting circuit which monitors whether the combined vibration mass give the first or second electrically equivalent impedance and provides a load detection signal only upon seeing the first electrically equivalent impedance. Also included in the device is a control circuit which limits or stops the electric pulse when the load detection signal is not received within a predetermined time period. The feature of the present invention resides in that the combined vibration mass has a structure that restrains vibrations at a center portion of the vibration mass in order to reduce a parasitic resonance, thereby differentiating the first electrically equivalent impedance from the second electrically equivalent impedance. Thus, the load detecting circuit can successfully judge whether the applicator head is in contact with or out of contact from the skin, whereby the control circuit can be made reliable to limit the ultrasonic vibrations from being generated when the applicator head is unloaded.

Preferably, the vibrator element is composed of a piezoelectric element in the form of a circular disc having flat upper and lower end faces provided respectively with upper and lower electrodes across which the electric pulse is applied. At least one of the upper electrode, the lower electrode, and the piezoelectric element has a center opening which is responsible for restraining the vibrations at the center of the combined vibration mass.

In addition to the center opening, at least one of the upper and lower electrodes may be dimensioned to have a diameter smaller than that of the piezoelectric element to leave the peripheral portion of the piezoelectric element uncovered also for reducing undesired vibrations around the periphery of the piezoelectric element.

Alternatively, at least one of the upper and lower electrodes is divided by at least one slit into a plurality of identical segments. The slit extends diametrically to leave the center and the diametrically extending band portion of the piezoelectric element uncovered for restraining the vibrations at the center of the vibration mass.

Instead of providing the diametrically extending slit, at least one of the upper and lower electrodes may be configured to have at least one slit that uncovers the center portion of the piezoelectric element for the same purpose of restraining the vibrations at the center of the vibration mass.

In combination with or separately from the provision of the center opening in at least one of the upper electrode, the lower electrode, and the piezoelectric element, the horn may be configured to have a center hole in the form of a through-hole or cavity for restraining the vibrations at the center of the vibration mass.

Further, instead of being formed with the center opening, the upper electrode may be covered with an elastic member that absorbs the vibrations at the center portion of the vibration mass for reducing the parasitic resonance.

Still further, the upper electrode may be covered on its center with a solder bulk for electrical connection of the upper electrode to a lead wire leading from the driver circuit. The solder bulk adds a weight to the center of the combined vibration mass for restraining the vibrations at the center portion thereof.

Further, the horn is preferred to be formed as an integral part thereof with a rim which surrounds the horn and which is adapted to secure the horn to the housing. Defined between the horn and the rim is a restrictor which restricts the ultrasound from propagating towards the rim, thereby concentrating the ultrasound to the horn for effectively transmitting the ultrasound to the skin through the horn. The restrictor may be in the form of a cavity formed along the boundary between the horn and the rim.

Preferably, the control circuit is designed to receive the first electrically equivalent impedance in order to vary the intensity of the ultrasound generated at the vibrator element in accordance with the magnitude of the first electrically equivalent impedance. As the first electrically equivalent impedance will vary depending upon a pressure at which the horn or the combined vibration mass is held against the user's skin, the device can vary the effect or the strength of the ultrasound being applied to the skin depending upon the pressure, thereby applying the ultrasound optimally to the user's skin for enhanced skin care result.

Still further, the device is preferred to include a motion detecting circuit which monitors whether the combined vibration mass is moving and provides a motion detection signal when the vibration mass is so moving. The control circuit is connected to receive the motion detection signal and controls the driver circuit to stop or limit the electric pulse when the motion detection signal is not continuous over a critical time duration even in the presence of the load detection signal being detected within the predetermined time period.

These and still other objects and advantageous features of the present invention will become more apparent from the following detailed description of the preferred embodiment when taken in conjunction with the attached drawings.

BEST MODE FOR CARRYING OUT THE INVENTION

Figure 1:
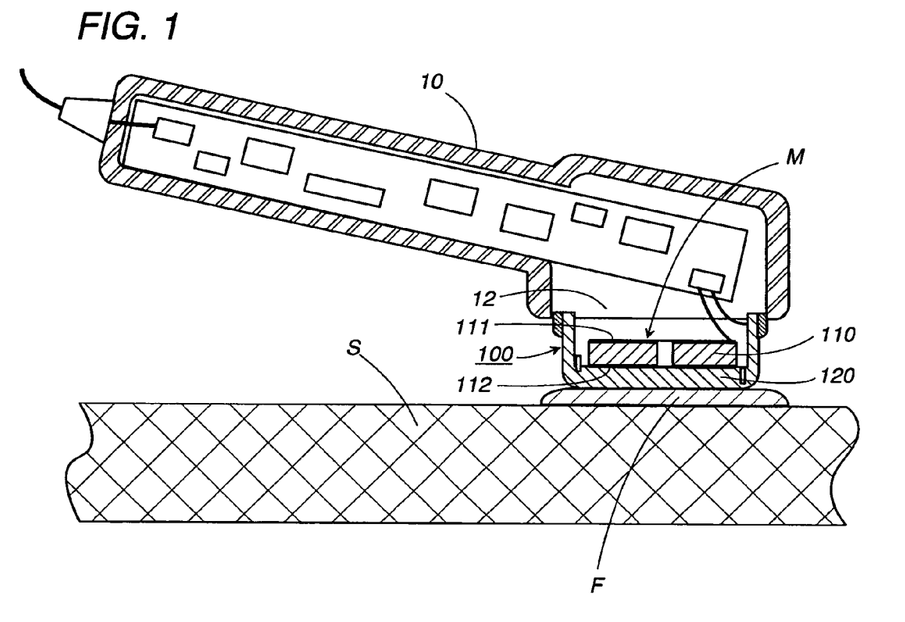
FIG. 1 is a front sectional view of an ultrasound applying skin care device in accordance with a preferred embodiment of the present invention.

FIG. 1 illustrates an ultrasound applying skin care device in accordance with a preferred embodiment of the present invention. The skin care device is utilized for face care or skin massage for enhancing the metabolism of a skin tissue for making the skin beauty and healthy. The device includes a hand-held grip housing 10 provided at its one end thereof with an applicator head 100 which is adapted in use to contact with a user's skin for applying ultrasound thereto. The applicator head 100 is composed of a vibrator element 110 in the form of a piezoelectric element generating the ultrasound, and a horn 120 transmitting the ultrasound to the skin S. The piezoelectric element is shaped into a circular disc having a flat upper surface and a flat lower surface which are covered respectively with upper and lower electrodes 111 and 112 across which an electric pulse is applied for generating the ultrasound vibration. The vibrator element 110 and the horn 120 are integrated into a combined vibration mass M which is caused by the electric pulse to resonate for generating and applying the resonant ultrasound vibration to the skin S. Preferably, the device is designed to generate the ultrasound having a frequency of 1 MHz to 10 MHz and transmitted to the skin at an intensity of 0.1 W/cm$^2$ to 2.0 W/cm$^2$. Further, it is preferred to use a gel or like fluid F at the interface between the horn and the skin for promoting the transmission of the ultrasound to the skin S.

Figure 2A:
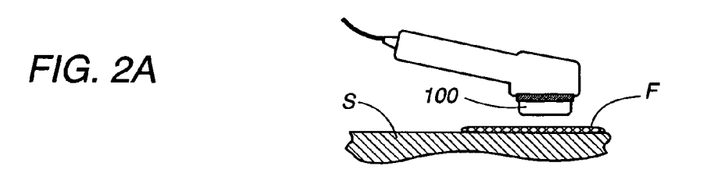
FIGS. 2A to 2C show improper use conditions of above device.
Figure 2B:
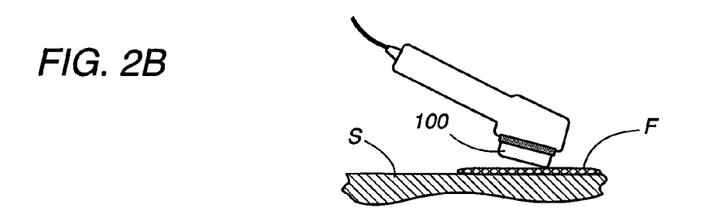
Figure 2C:
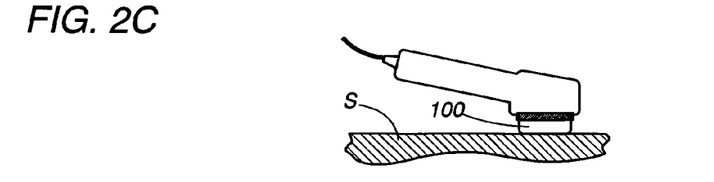

As will be explained later in details, the device is equipped with a safe-guard for limiting or stopping the ultrasonic vibrations being transmitted to the skin when the applicator head 100 is not in a normally loaded condition of FIG. 1, i.e., the applicator head is held in any one of improper conditions. As shown in FIGS. 2A to 2C, the improper conditions include an unloaded condition where the applicator head 100 is away from the skin (FIG. 2A), a partial contact condition where the applicator head 100 is placed only partially against the skin (FIG. 2B), and a direct contact condition where the applicator head 100 is placed against the skin without using the fluid F at the interface therebetween (FIG. 2C).

Figure 3:
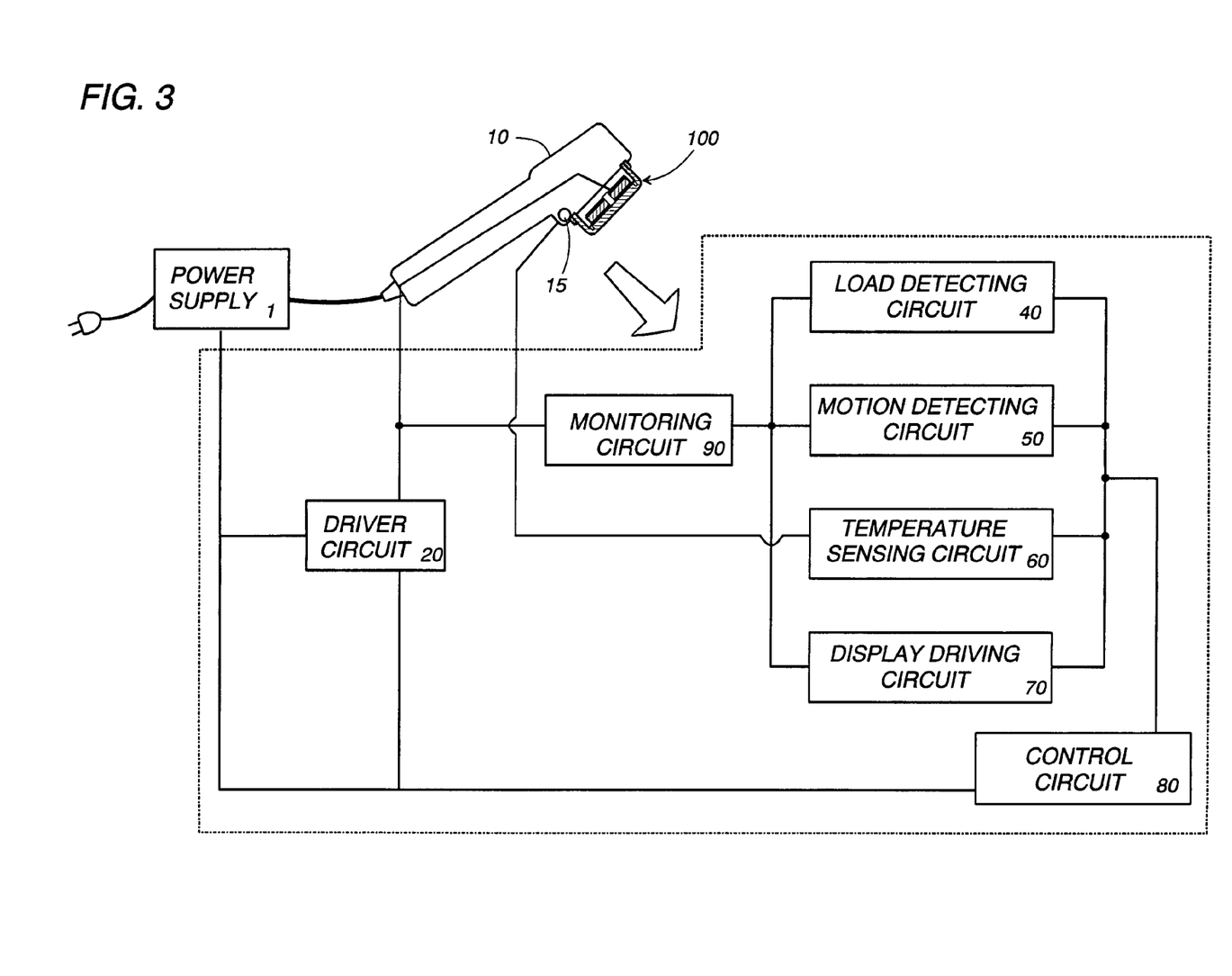
FIG. 3 is a block diagram of an electric circuitry of the above device.

As shown in FIG. 3, the device includes a driver circuit 20 for providing the electric pulse across the electrodes 111 and 112 of the piezoelectric element 110, a load detecting circuit 40 for detection a load condition of the applicator head 100, a motion detecting circuit 50 for detection of a motion of the applicator head 100, a temperature sensing circuit 60 for sensing a temperature of the piezoelectric element 110, a display driver circuit 170 for displaying operating conditions of the device, and a control circuit 80 for control of the above circuits. The driver circuit 20 is energized by a power supply 1 accommodated within a separate power pack 2 for converting a commercial AC line voltage into a DC voltage. Also included in the device is a monitoring circuit 90 for monitoring the ultrasound being generated and applied to the user's skin based upon an electrically equivalent impedance of the combined vibration mass M.

The device 10 is designed to generate the ultrasound while the horn 120 is kept substantially in contact with the use's skin. For this purpose, the load detecting circuit 40 is provided to detect whether a suitable load is applied as a consequence of the horn 120 being in contact with the user's skin via the fluid F. When the horn 120 is not in contact with the skin and fails to transmit the ultrasound successfully, the load detecting circuit 40 determines that the horn 120 or the vibration mass M is not loaded and restricts the generation of the ultrasound. The details of the load detection realized in the present invention will be discussed later. In use, it is desirable to move the applicator head 100, i.e., the combination mass slowly across the skin when applying the ultrasound. Otherwise, when the applicator head 100 stays at a portion over a long period, there is a potential hazard of causing a cold burn in the skin. In view of this, the motion detecting circuit 50 is provided to enable the continuous ultrasound application when the applicator head 100 is moving at a suitable rate and otherwise disable or limit the ultrasound generation. In addition, the control circuit 80 includes a timer which stops generating the ultrasound after the device is utilized over a preset time. That is, the timer will count a time only when the load detection signal from the load detecting circuit 40 indicates that the applicator head 100 is kept in the normal contact with the skin and when the motion detection signal from the motion detecting circuit 90 indicates that the applicator head 100 does not stay at a portion over a long time. The timer operates to continue generating the ultrasound over the preset time. Also, after the preset time is elapsed, the control circuit 80 gives an instruction to stop providing the electric power to the driver circuit 20, ceasing the ultrasound generation.

When the vibration mass suffers from abnormal vibrations with an attendant temperature rise due to malfunction of the driver circuit 20 or the like, the temperature sensing circuit 60 is responsive to an output from a temperature sensor 15 located adjacent the horn 120 for providing an output indicative of abnormal temperature rise to the control circuit 80 which in turn responds to stop the driver circuit 20.

Figure 4:
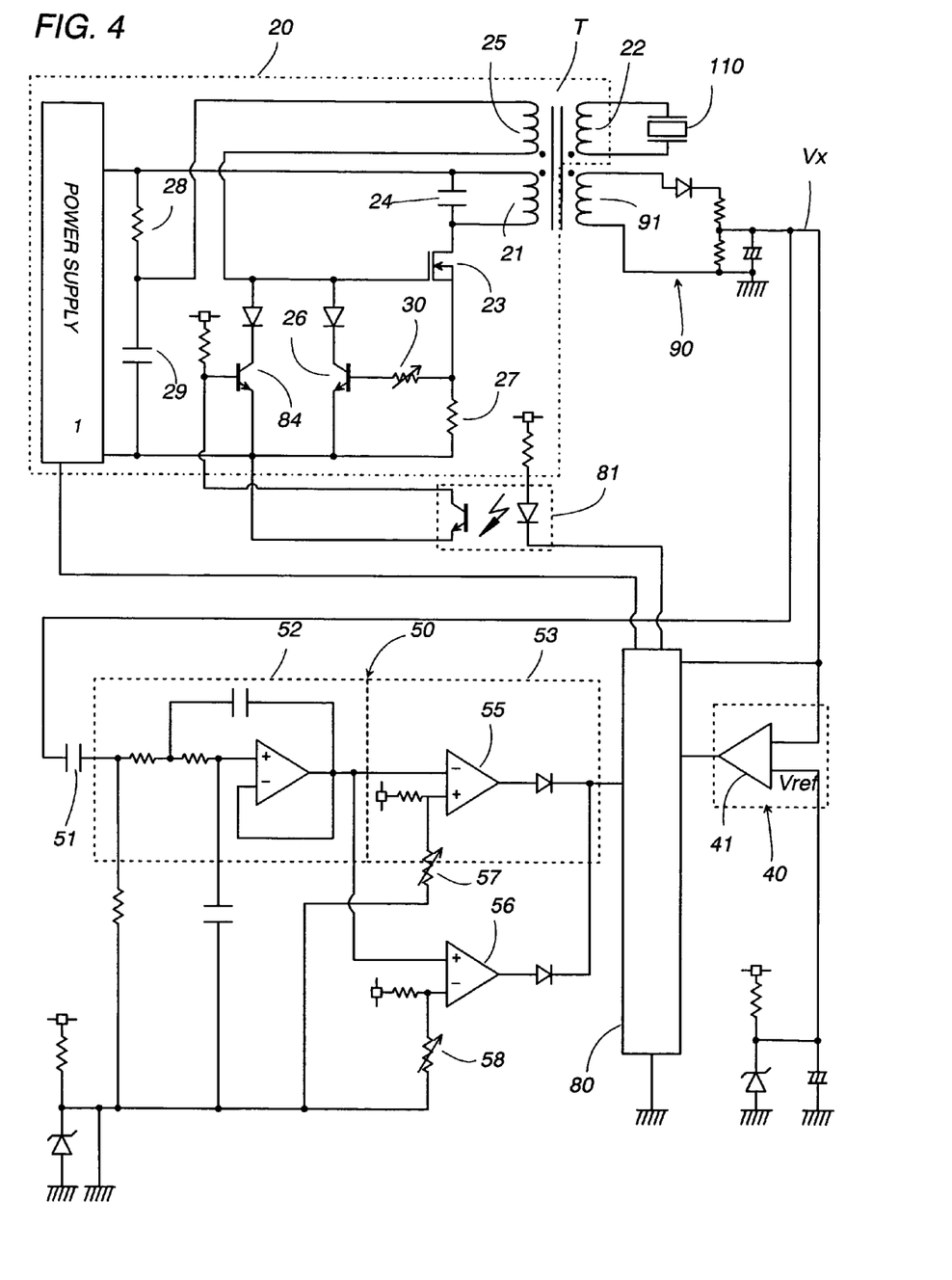
FIG. 4 is a circuit diagram illustrating a driver circuit, a load detecting circuit, a motion detecting circuit of the above circuitry.

As shown in FIG. 4, the driver circuit 20 includes an inverter which converts DC voltage from the power supply 1 into an AC voltage. Provided at the output end of the inverter is a transformer T with a primary winding 21 and a secondary winding 22. The primary winding 21 is connected in series with FET 23 and a current sensing resistor 27 across the power supply 1, and is cooperative with a capacitor 24 to form a parallel resonant circuit which provides a resonant voltage across the primary winding 21 upon turning off of FET 23. The piezoelectric element 110 is connected across the secondary winding 22 so as to effect the ultrasound vibrations by the AC voltage or the electric pulse induced at the secondary winding 22. A feedback winding 25 is coupled to the primary winding 21 to feedback the output of the driver circuit to FET 23. A bipolar transistor 26 is connected in a gate-emitter path of FET 23 for control of FET 23. Connected across the power supply 1 is a series combination of a starting resistor 28 and a capacitor 29 of which connection is connected through the feedback winding 25 to a gate of FET 23 to give a bias thereto. When capacitor 29 is charged by the power supply 1 to develop a voltage reaching a threshold of FET 23, FET becomes conductive to lower the drain voltage of FET 23. At this time, the feedback winding 25 generates a feedback voltage applied to the gate of FET 23, thereby increasing the current flowing through the FET. Subsequently when a voltage developed across current sensing resistor 27 reaches a predetermined level in correspondence to the increasing current through FET, transistor 26 becomes conductive to turn off FET 23. Whereby, the resonant circuit of primary winding 21 and capacitor 24 becomes active to make a resonance. At the end of one cycle of the resonance, the feedback voltage induced at feedback winding 25 reaches a voltage of turning on the gate of FET 23, thereby again making the FET conducive. The above operations are repeated to maintain the resonant voltage or the electric pulse so as to oscillate the piezoelectric element 110. The frequency of the resonant circuit is set variable in the range of 1 MHz to 10 MHz.

Figures 5A, 5B:
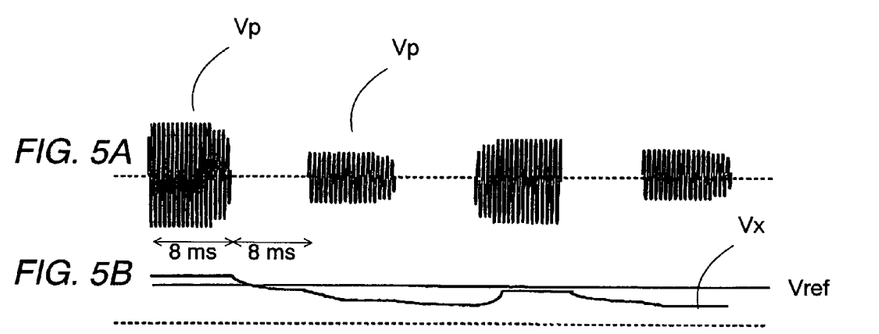
FIGS. 5A to 5F are waveform charts illustrating the operation of the load detecting circuit and the motion detecting circuit.
Figure 5C:
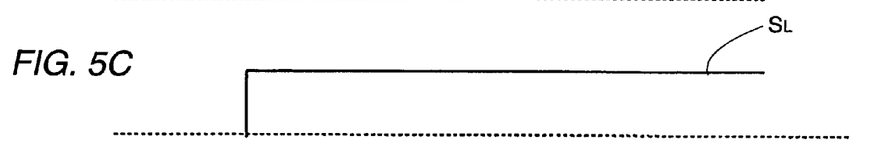

Connected between the base of transistor 26 and resistor 27 is a variable resistor 30 of which value is varied in order to adjust a timing of turning on transistor 26 for regulating the resonant frequency. It is noted in this connection that the resonant circuit is controlled by the control circuit 80 to give an intermittent oscillation having a rest period between adjacent pulse series Vp, as shown in FIG. 5A.

The transformer T includes an auxiliary winding 91 which is cooperative with a rectifier circuit that rectifies the output of auxiliary winding 91 to constitute the monitoring circuit 90 which gives a monitoring output indicative of a condition of the ultrasound being applied to the user's skin. The monitoring output Vx includes low frequency components which are given as a result of moving the applicator head 100 and of which frequency is lower than that of the ultrasonic vibration. More precisely, the voltage appearing across auxiliary winding 91 includes low frequency components originating from a variation in electrically equivalent impedance of the combined vibration mass M upon contact with the load and originating from rubbing sounds appearing in response to the applicator head 100 moving across the skin of the user's skin, in addition to high frequency components indicative of the ultrasound vibrations. The monitoring output Vx is obtained by rectification of voltage appearing across auxiliary winding 91, and is fed to the load detecting circuit 40 and the motion detecting circuit 50 for making the load detection and the motion detection.

The load detecting circuit 40 has a comparator 41 which compares the monitoring output Vx from the monitoring circuit 90 with a reference level Vref. The monitoring output Vx has a waveform pattern as shown in FIG. 5B. When the output Vx becomes lower than the reference level Vref, the comparator 41 provides a H-level load detection signal SL to the control circuit 80 as indicative of that the applicator head 100 is kept in the normal contact with the user's skin. When the load detection signal SL is not acknowledged continuously over a predetermined time period, the control circuit 80 stops operating the driver circuit 20 or disables the power supply 1. In this embodiment, the load detection signal SL is generated when the monitoring output Vx is lower than the reference level Vref in consideration of that the resonant voltage is lowered by the presence of the load, i.e. the increased impedance of the combined vibration mass M.

In addition, the output Vx indicative of the impedance of the combined vibration mass M is fed also to the control circuit 80. When the output Vx is equal to the reference level Vref or greater, the control circuit 80 operates to vary the output voltage of the power supply 1 a reverse proportion to the magnitude of the output Vx. That is, the combined vibration mass M is held against the user's skin at a greater pressure, the control circuit 80 acts to lower the intensity of the ultrasound being applied to the skin, and vice versa. With this result, the ultrasound can be adjusted depending upon the pressure at which the combined vibration mass M is held against the skin, thereby transmitting the ultrasound at an optimal intensity for enhanced skin care effect.

It is possible that a resonant circuit of different configuration may vary the impedance characteristic of the combined vibration mass M in order to break the impedance matching with the resonant circuit, thereby causing the monitoring output to increase in the presence of the load. In this case, it is made to provide the load detection signal SL when the monitoring output Vx exceeds the reference level Vref. Also, it is equally possible to limit or reduce the ultrasound energy upon detection of the no-load condition, and also to vary the ultrasound energy depending upon the magnitude of the monitoring output.

Figures 5D, 5E:
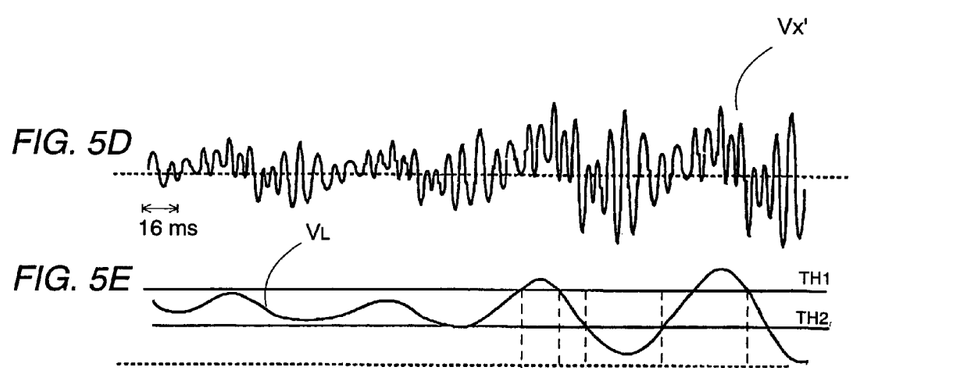
Figure 5F:
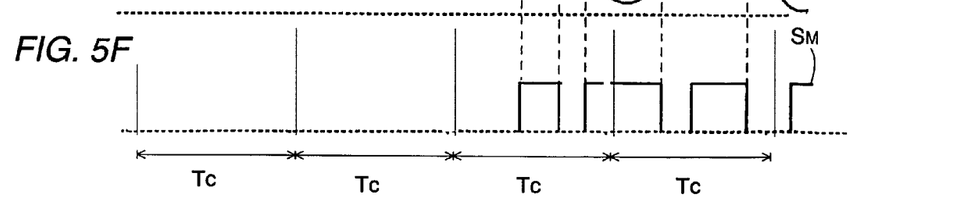

Further, the monitoring output Vx is fed through a capacitor 51 to the motion detecting circuit 50 in the form of an output Vx', as shown in FIG. 5D. The motion detecting circuit 50 includes a low-pass filter 52 and a judging circuit 53. The output Vx' is removed of high frequency components through the filter 52 to give a low frequency output VL free from the components not caused by the motion of the applicator head 100, as shown in FIG. 5E. Thus obtained low frequency output VL is fed to two comparators 55 and 56 of the judging circuit 53 and compared respectively with individual thresholds TH1 and TH2 (TH1>TH2) to provide to the control circuit 80 a H-level motion detection signal SM (shown in FIG. 5F) over a period in which the output VL is higher than the threshold TH1 or lower than the threshold TH2. TH1 and TH2 can be adjusted by variable resistors 57 and 58. The control circuit 80 counts the time period of the H-level motion detection signal SM within a predetermined duration Tc (for example, 15 seconds) and determines that the applicator head 100 has moved suitably when the sum of the counted times within the duration Tc exceeds a predetermined reference. Otherwise, the control circuit 80 determines that no suitable motion has been made and provides a limit signal of limiting the driver circuit 20.

The driver circuit 20 includes a transistor 84 which is connected in parallel with transistor 26 across gate-source path of FET 23 and which is connected to the control circuit 80 through a photo-coupler 81. Thus, upon receiving the limit signal from the control circuit 80, the transistor 84 is turned on to thereby turn off FET 23 for disabling the driver circuit 20. Although the limit signal acts to stop the driver circuit 20 in this embodiment, the present invention is not limited to this feature and may be arranged to control the driver circuit 20 or power supply 1 to reduce the ultrasonic vibration energy.

Figure 6:
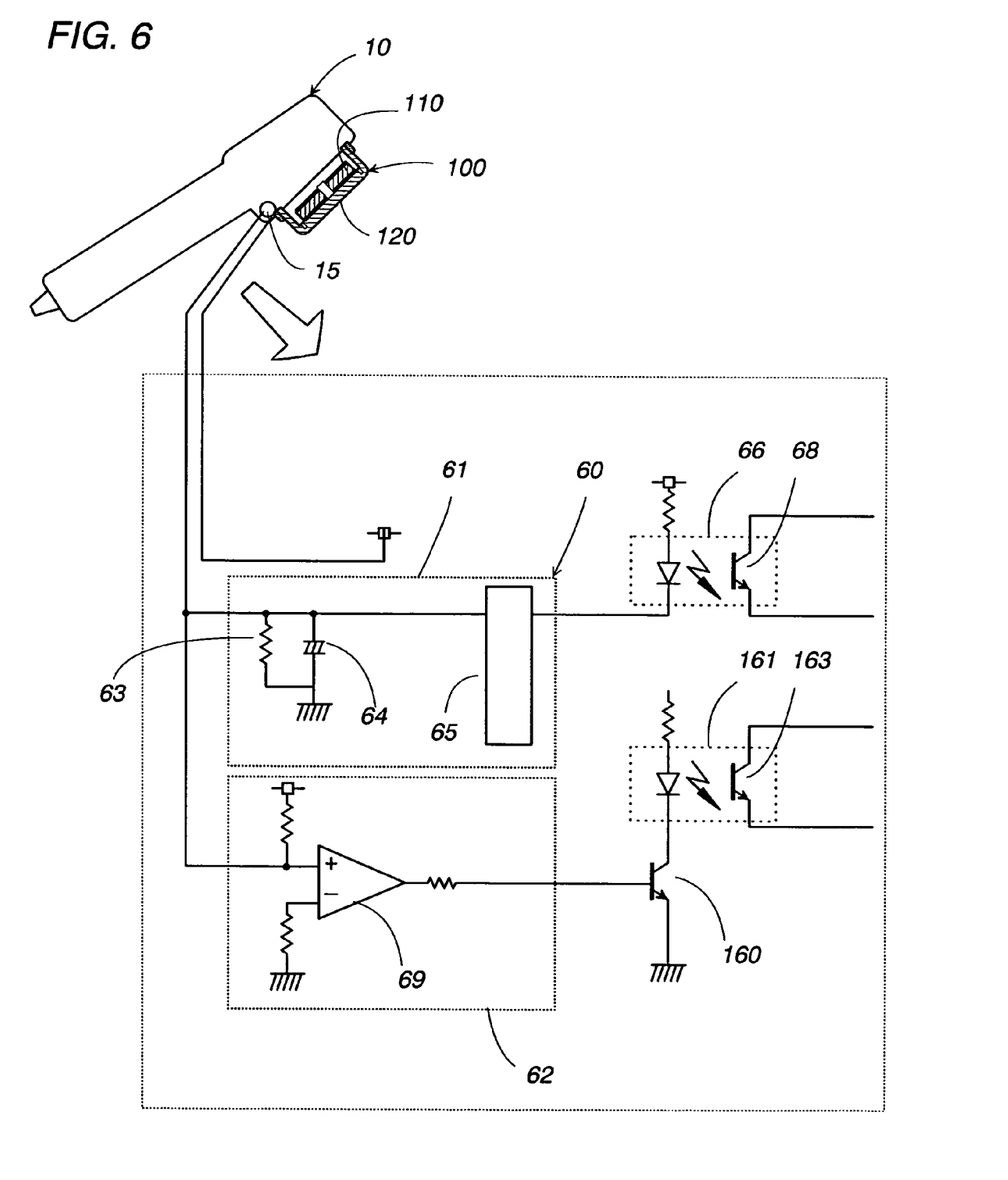
FIG. 6 is a circuit diagram illustrating a temperature sensing circuit of the above circuitry.

As shown in FIG. 6, the temperature sensing circuit 60 includes a first temperature sensing unit 61 and a second temperature sensing unit 62 both receiving an output from a thermistor 15 for temperature sensing. First temperature sensing unit 61 has a temperature controller 65 to which the output from thermistor 15 is fed through a resistor 63 and a capacitor 64. When the temperature sensed at thermistor 15 is found to exceed a predetermined reference temperature, the temperature controller 65 issues a stop signal to the driver circuit 20 through a photo-coupler 66. The photo-coupler 66 has a transistor 68 which is connected in a base-emitter path of the transistor 84, so that the stop signal causes the transistor 84 to turn on for stopping the oscillation of the driver circuit 20. A hysterics is given to the temperature control such that, after the temperature of the horn 120 sensed by thermistor 15 goes high above the reference temperature, the driver circuit 20 is enabled to resume the oscillation only after the sensed temperature goes below a temperature level which is lower than the reference temperature. When the sensed temperature goes below the temperature level, the temperature controller 65 responds not to issue the stop signal, thereby resuming the oscillation at the driver circuit 20. The second temperature sensing unit 62 includes a comparator 69 which operates to turn on a transistor 160 when the temperature sensed at thermistor 15 exceeds a predetermined reference, thereby turning on a transistor 163 of a photo-coupler 161 and consequently disabling the power supply 1 connected to transistor 163. The predetermined reference for the comparator 69 is set to be higher than the reference temperature of the temperature controller 65 for stopping the ultrasonic oscillation as a safeguard in response to the horn 120 being abnormally heated even if the temperature controller 65 made of a microprocessor should fail to operate.

Figure 7:
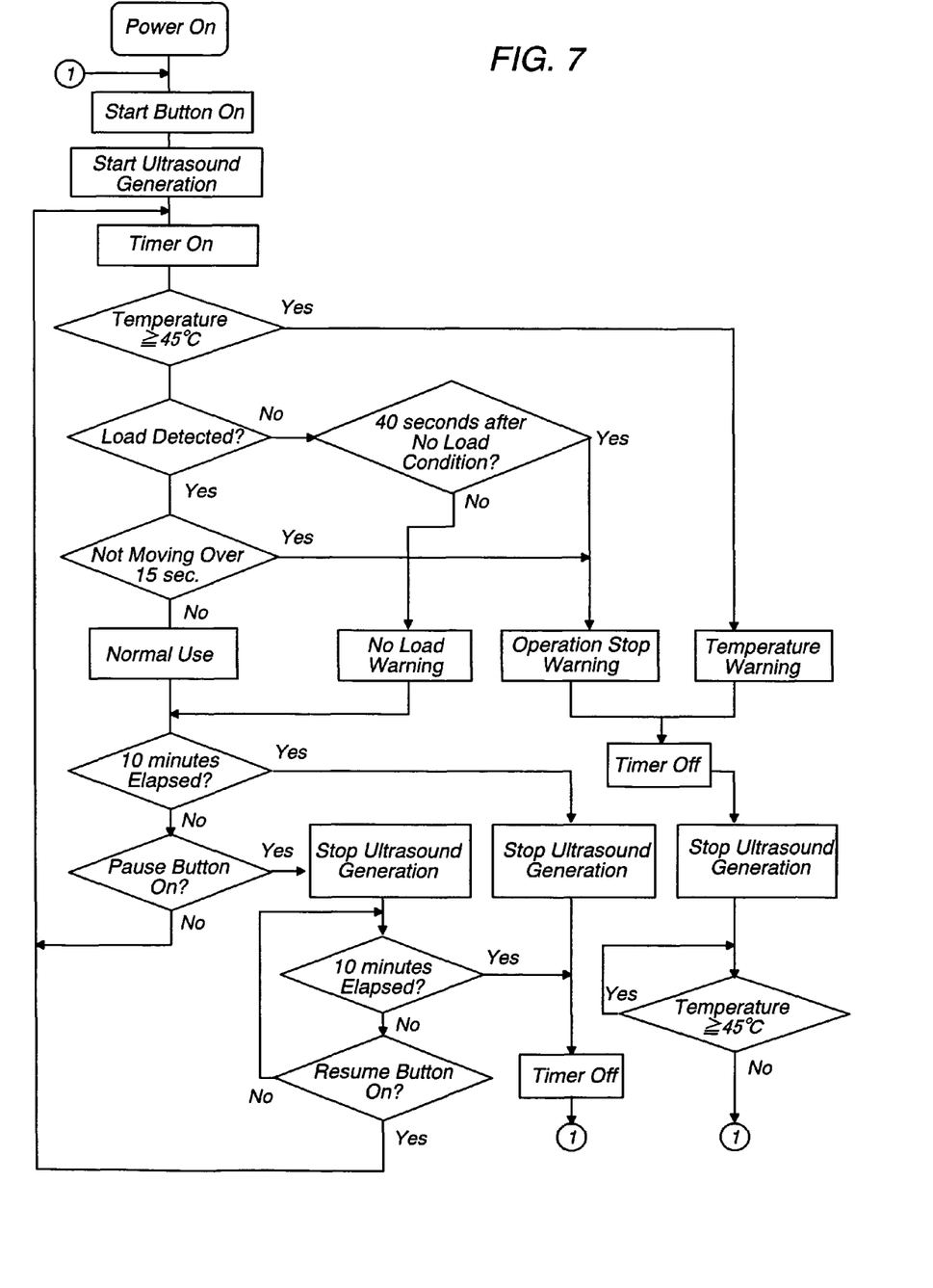
FIG. 7 is a flow chart illustrating the operations of the device.

Operation of the ultrasound applying device is now explained with reference to FIG. 7. After turning on a power switch, pressing of a start button actuates the driver circuit 20, causing the piezoelectric element 110 to start generating the ultrasound, and starting the timer. At this time, the temperature sensing is made for the horn 120 so that when the first temperature sensing unit 61 sees the temperature exceeding, for example, 45°, the display driving circuit 70 gives the temperature warning that the horn 120 is over-heated, and causing the timer as well as the driver circuit 20 to stop. When the sensed temperature is found to be less than 45° C. at a step after starting the timer, the load detection is available, and subsequently the motion detection is available provided that the load detection signal is issued as indicative of that the applicator head 100 is loaded. When no load detection signal is issued, a no-load warning is displayed for a limited time period of 40 seconds, for example, prompting the user to make the applicator head 100 in contact with the skin. After elapse of 40 seconds with no load detection signal, a control is made to display a warning of stopping the operation and stop the timer and the ultrasound generation. The motion detection is made in the presence of the load detection signal so that, when the motion detection signal is issued within, for example, 15 seconds, a display of normal operation is made and a count-down instruction is given to the timer. After the elapse of a predetermined operation time, say, 10 minutes in this condition, the driver circuit is stopped. When a pause button is pressed within 10 minutes, the driver circuit is stopped but with the timer operating continuously to count down. When a restart button is pressed within the 10 minutes, the driver circuit resumes generating the ultrasound.

Although the above embodiment is so designed that the control circuit disables the driver circuit when no load or no motion is detected, the present invention is not limited to this feature and is designed to reduce the ultrasound energy upon such detection.

Figure 8:
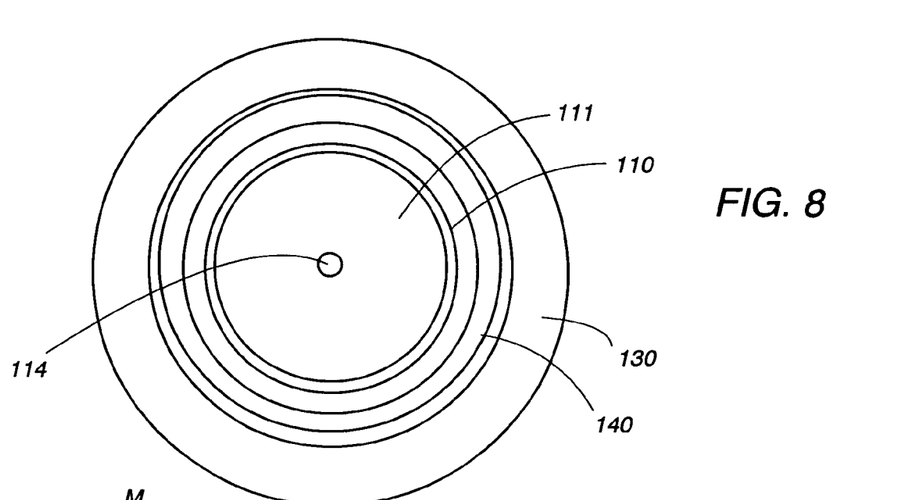
FIG. 8 is a top plan view of an applicator head of the above device.
Figure 9:
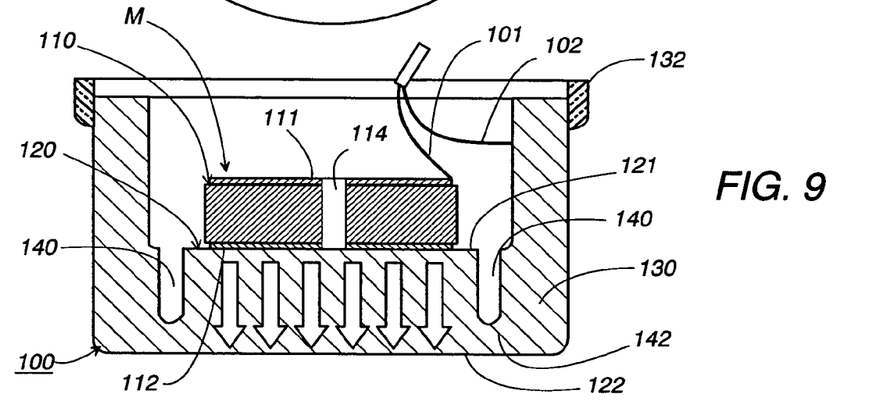
FIG. 9 is a sectional view of the applicator head.
Figure 10:
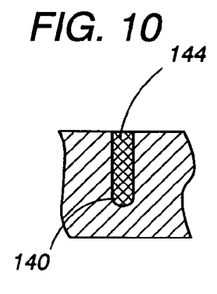
FIGS. 10 to 12 are partial views illustrating modified structure of the applicator head.
Figure 11:
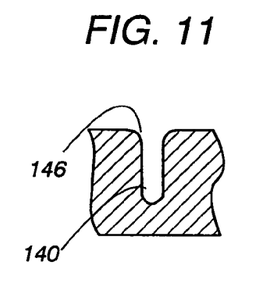
Figure 12:
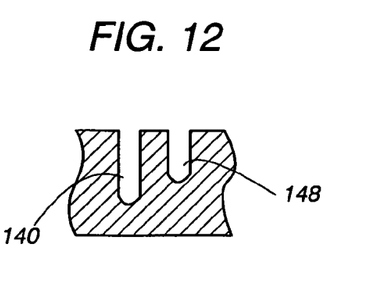

Now referring to FIGS. 8 and 9, the details of the applicator head 100, i.e., the combination of the piezoelectric element 110 and the horn 120 will be discussed. The piezoelectric element 110 is made of a ceramic and shaped into the circular disk having a uniform thickness and being provided on its upper and lower faces respectively with the upper and lower electrodes 111 and 112. The horn 120 is made of aluminum and is shaped into a circular disk having a surface area slightly larger than the piezoelectric element 110 and having a uniform thickness. The electric pulse from the driver circuit 20 is applied across the electrodes 111 and 112 by way of lead wires 101 and 102 respectively soldered to the upper electrode 111 and the horn 120, as shown in FIG. 9. The horn 120 is formed as an integrally part thereof with a tubular rim 130 which surrounds the horn 120. The rim 130 projects upwardly from the periphery of the horn 120 and is secured at its upper end to the housing 10 to support the applicator head 100 to the housing. The upper end of the rim 130 fits snugly into a mouth 12 of the housing 10 with an elastic damper ring 132 interposed therebetween. The horn 120 has a flat mounting face 121 for carrying thereon the piezoelectric element 110 in an intimate contact relation, and a flat skin opposing face 122 for contact with the skin through the fluid F spread on the skin S. The piezoelectric element 110 is secured to the horn 120 such that they are integrated into the combined vibration mass M which resonates with the electric pulse from the driver circuit 20 to generate the ultrasound to be transmitted to the skin. A restrictor 140 in the form of a cavity extends between the horn 120 and the rim 130 in order to restrict the ultrasound vibrations from propagating towards the rim 130, thereby concentrating the ultrasound effectively to the user's skin, as indicated by arrows in FIG. 9. That is, the cavity 140 acts to isolate the rim 130 substantially from the combined vibration mass M of the piezoelectric element 110 and the horn 120 with regard to the ultrasound vibrations. As a result of forming the cavity 140, a bridge 142 of reduced thickness remains for connection of the horn 120 and the rim 130. The reduced thickness (t) of the bridge 142 is selected to be other than an integral multiple of one-fourth of the wavelength of the ultrasound ($t \neq n \cdot \lambda/4$, where n is an integer)) for effectively restricting the ultrasound vibrations from propagating towards the rim 130. As shown in FIGS. 10 and 11, the cavity 140 may be filled with a suitable medium 144 for blocking the ultrasound vibrations, or may be finished with rounded edges 146. Further, as shown in FIG. 12, an additional cavity 148 of different depth may be formed in a concentric relation to the cavity 140.

Figure 13:
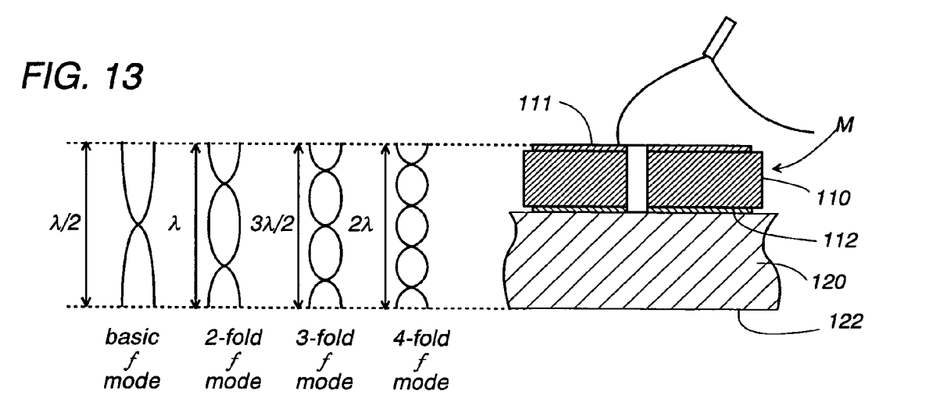
FIG. 13 is a schematic view illustrating a relation between the wavelength of the ultrasound of different frequencies and a combined vibration mass of the applicator head.

As shown in FIG. 13, the total thickness (T) of the combined vibration mass M of the piezoelectric element 110 and the horn 120 is selected to be half of wavelength ($T=\lambda/2$) of the ultrasound vibrating at a basic frequency of, for example, 1 MHz so that the combined vibration mass M can resonate also at the frequencies that are integral multiples of the basic frequency, for example, 2-fold, 3-fold, and 4-fold of the basic frequency, while forming antinodes at the skin opposing face 122 of the horn 120 and at the upper surface of the electrode 111, as schematically seen in the figure.

Figure 14:
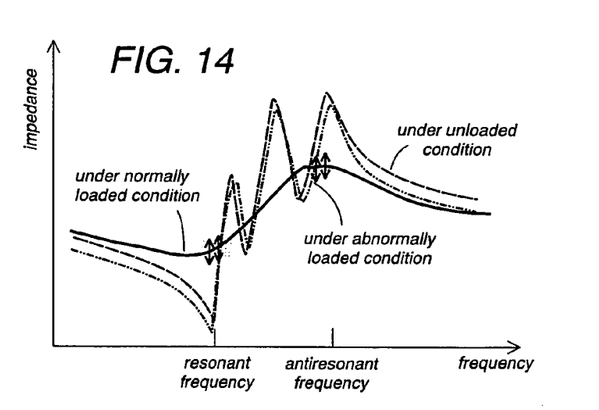
FIG. 14 is a graph illustrating, as a comparative purpose, electrically equivalent impedances of the vibration mass given under a normally loaded condition, an unloaded condition, and an abnormally loaded condition, respectively, without a structure of reducing a parasitic resonance.

In order to transmit the ultrasound power effectively to the skin at a minimum loss and also to discriminate the normally loaded condition from an abnormally loaded or the unloaded condition when actuating the combined vibration mass M around the resonant frequency, the piezoelectric element 110 is designed to have a structure that restrains vibrations at the center of the combined vibration mass M for reducing an undesired parasitic resonance which would otherwise makes the load detecting circuit 40 difficult to distinguish the normally loaded condition from the unloaded or abnormally loaded condition. That is, as shown in FIG. 14, the parasitic resonance brings about fluctuations which are superimposed on the electrically equivalent impedance curves as indicated by dotted lines with respect to varying frequency when the vibration mass M is under the unloaded condition or the abnormally loaded condition. With this result, it becomes practically difficult to distinguish the normally loaded condition from the unloaded or abnormally loaded condition on the basis of the impedance of the vibration mass M in the vicinity of the resonant or antiresonant frequencies. Consequently, it becomes hardly possible to extract the varying impedance indicating the contacting pressure of the vibration mass M within an admissible range as indicated by arrowed lines in the figure in the vicinity of the resonant or antiresonant frequencies, failing to vary the intensity of the ultrasound in accordance with the pressure at which the combination mass M is held against the user's skin, while the vibration mass M is in the normally loaded condition.

Figure 15:
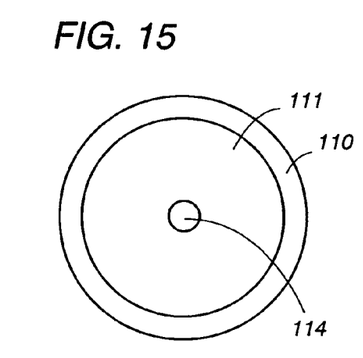
FIG. 15 is a top plan view of the vibrator element.
Figure 16:
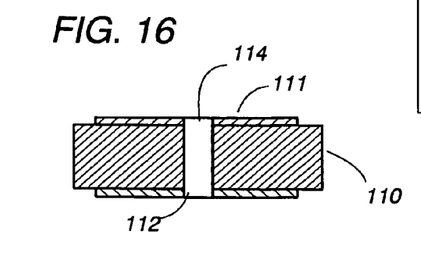
FIG. 16 is a sectional view of the vibrator element.

FIGS. 15 and 16 show one preferred structure for reducing the undesired parasitic resonance to such an extent that the load detecting circuit 40 can discriminate the normally loaded condition from the unloaded or abnormally loaded condition with reference to the electrically equivalent impedance of the combined vibration mass M. In this structure, a center opening 114 is formed to extend the center of the upper electrode 111, the piezoelectric element 110, and the lower electrode 112 for restraining the vibrations at the center of the piezoelectric element 110 and therefore the vibration mass M. With this result, the combined vibration mass M exhibits definite impedance characteristic curves in relation to the frequency under the unloaded or abnormally loaded condition, as indicated by dotted lines in FIG. 17, that can be well distinguished from the impedance curve that the vibration mass exhibits under the normally loaded condition, as indicated by solid line indicated in the same figure.

Figure 17:
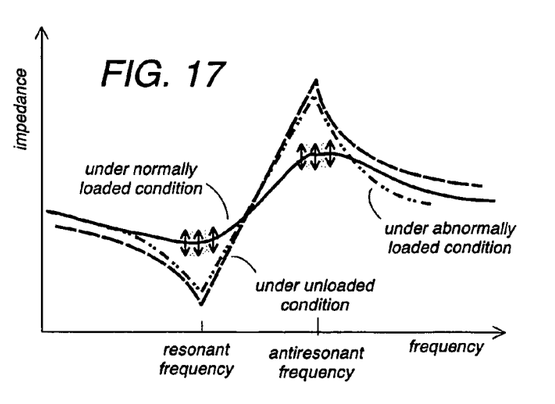
FIG. 17 is a graph illustrating the electrically equivalent impedances of the vibration mass given under the normally loaded condition, the unloaded condition, and the abnormally loaded condition, respectively, for the combined vibration mass in accordance with the embodiment of the present invention.

As apparent from FIG. 17, when subject to the unloaded or abnormally loaded condition, the vibration mass M can give the electrically equivalent impedance which are well distinctive from the impedance given under the normally loaded condition. By taking the advantage of the distinction, the load detecting circuit 40 can discriminate the abnormally loaded or unloaded condition successfully simply by monitoring the voltage reflecting the electrically equivalent impedance of the vibration mass M, as explained hereinbefore with reference to the monitoring circuit 90. In this consequence, it becomes possible to extract the impedance varying with the contacting pressure of the vibration mass M within the admissible range as indicated by arrowed lines in the figure in the vicinity of the resonant or antiresonant frequencies. Whereby, it can be made to vary the intensity of the ultrasound in accordance with the pressure at which the combination mass M is held against the user's skin, as long as the vibration mass M is in the normally loaded condition.

Figure 18:
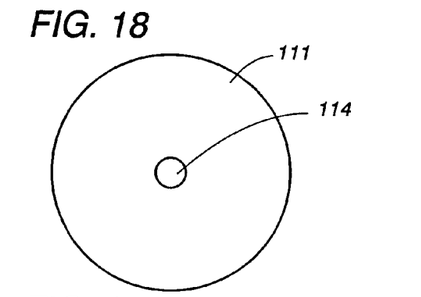
FIGS. 18 and 19 are top and sectional views of the vibrator element in accordance with a modification of the above embodiment.

In combination with the center opening 114, at least one of the upper and lower electrodes 111 and 112 may be shaped to have a diameter smaller than that of the piezoelectric element 110 to reduce the vibrations also at the periphery of the piezoelectric element and therefore the combined vibration mass M for further reducing the parasitic resonance. The center opening 114 may be formed in at lease one of the electrodes and the piezoelectric element, for example, as shown in FIGS. 18 and 19.

Figures 19, 21, 22, 23, 24, 25, 26, 27:
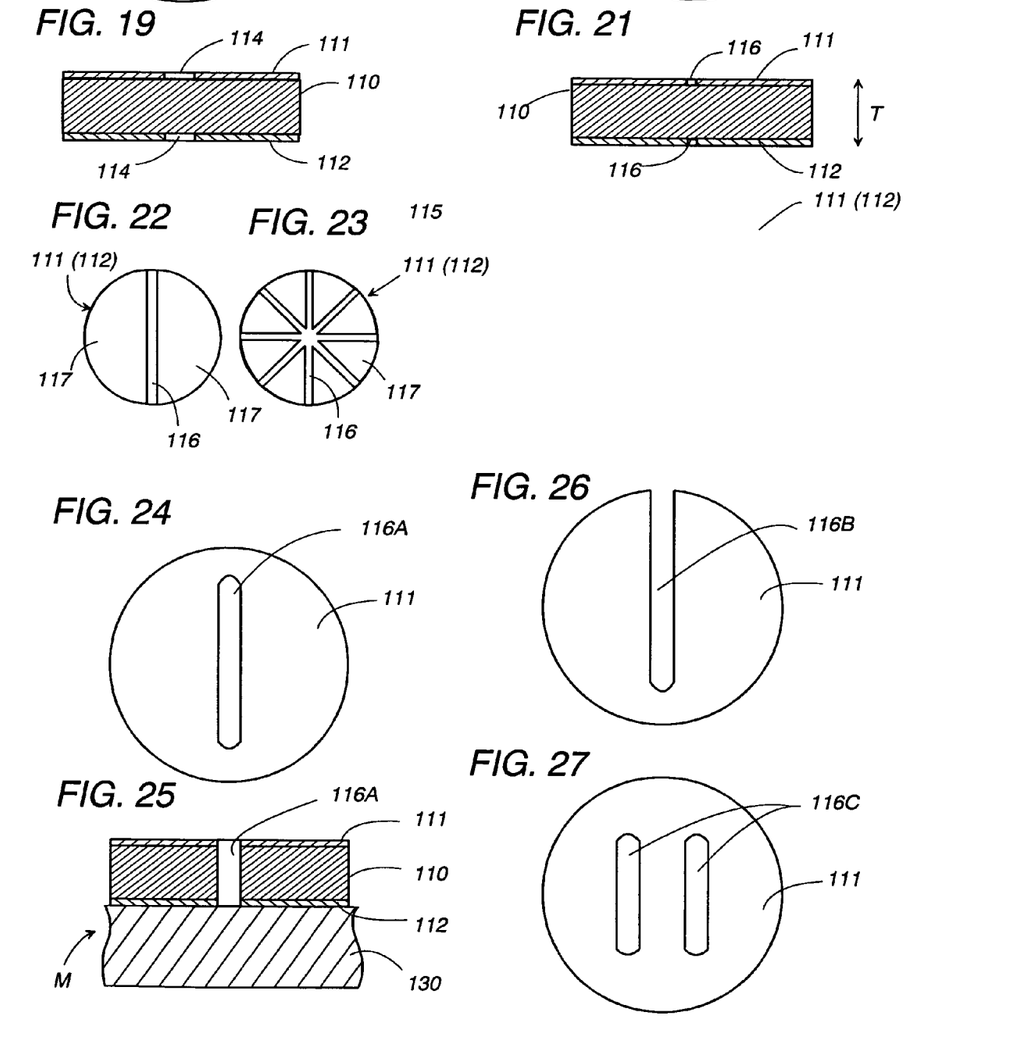
FIGS. 20 and 21 are top and sectional views of the vibrator element in accordance with another modification of the above embodiment.
FIGS. 22 and 23 are top views illustrating further modifications of the above embodiment.
FIGS. 24 and 25 are top and sectional views of the vibrator element in accordance with a still further modification of the above embodiment.
FIGS. 26 and 27 are top view illustrating further modifications of the above embodiment.
Figure 20:
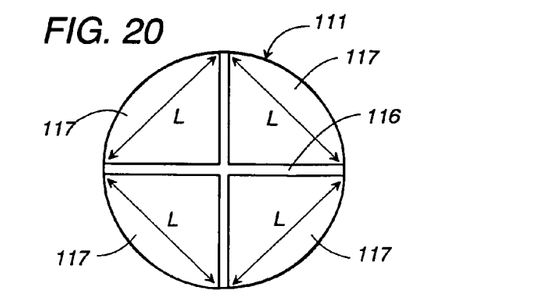

Further, as shown in FIGS. 20 and 21, the electrodes 111 and 112 may be divided by diametrically extending slits 116 into four identical segments or sectors 117. The slits extend through the center of the electrodes to leave the center and the diametrically extending band portion of the piezoelectric element uncovered, thereby restraining the vibrations at the uncovered center and the band portions and therefore reducing the undesired parasitic resonance in order to realize the impedance characteristic of FIG. 17 as well.

Alternatively, one or both of the electrodes 111 and 112 may be divided into two or eight segments 117, as shown in FIGS. 22 and 23 for the same purpose.

Further, it is possible to give a slit 116A with closed ends also in the piezoelectric element 110 and the electrodes 111 and 112, as shown in FIGS. 24 and 25, or to give a slit 116B open at its one end, or to give parallel slits 116C, as shown in FIGS. 26 and 27, in at least one of the electrodes and the piezoelectric element.

Figure 28:
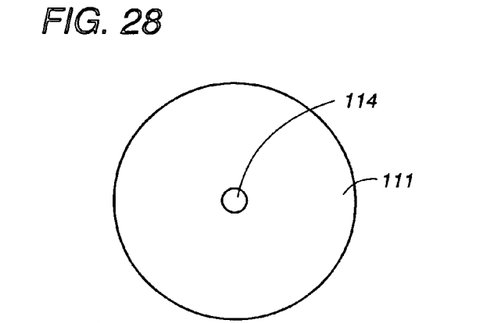
FIGS. 28 and 29 are top and sectional views of the vibrator element in accordance with a more modification of the above embodiment.
Figure 29:
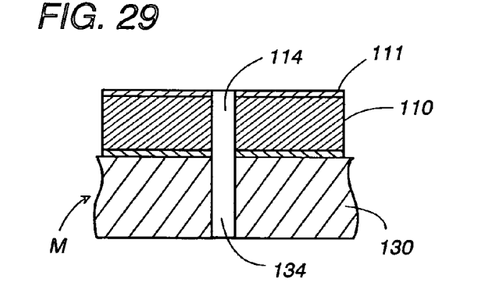
Figure 30:
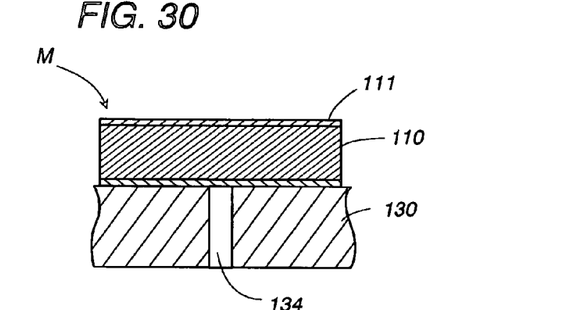
FIGS. 30 and 31 are sectional views illustrating modifications of the above embodiment.
Figure 31:
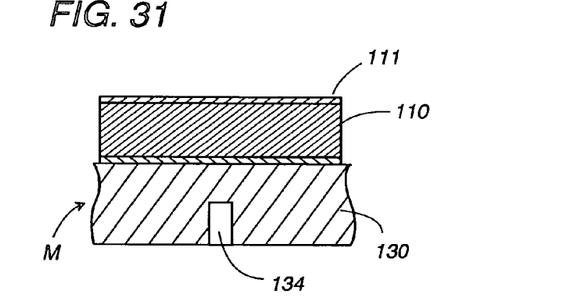

FIGS. 28 and 29 show a modification of the above embodiment in which a center hole 134 is formed in the horn 120 in alignment with the center opening 114 for further restraining the vibrations at the center of the combined vibration mass M and therefore reducing the undesired parasitic resonance to a large extent. The combination mass M may be provided only with the center hole 134 in the horn 120, as shown in FIG. 30, In this instance, the center hole 134 may be in the form of a cavity, as shown in FIG. 31.

Figure 32:
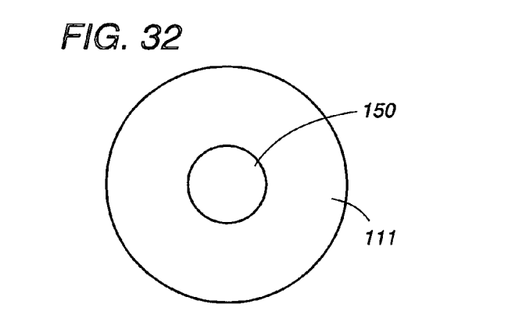
FIGS. 32 and 33 are top and sectional views of the vibrator element in accordance with a further modification of the above embodiment.
Figure 33:
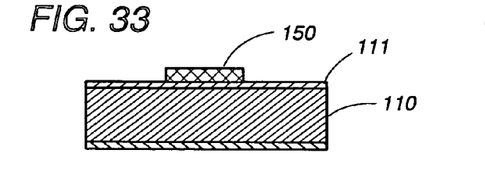
Figure 34:
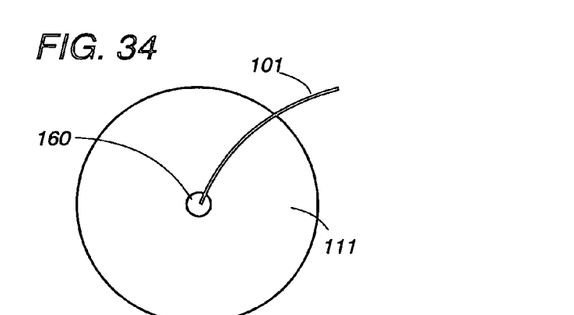
FIGS. 34 and 35 are top and sectional views of the vibrator element in accordance with a more modification of the above embodiment.
Figure 35:
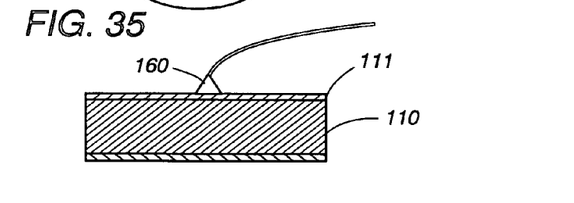

FIGS. 32 and 33 show an alternative structure in which an elastic member 150 is secured on the center of the upper electrode 111 for absorbing and therefore restraining the vibrations at the center of the piezoelectric element 110. The elastic member 150 is preferably made of a silicone rubber. Instead of providing the elastic member 150, it is equally possible to give a weight on the center of the electrode 111 for restraining the vibrations at the center of the piezoelectric element 110 and therefore reducing the undesired parasitic resonance at the center of the combined vibration mass M. The weight is given by a solder bulk 160 or land used for electrical connection of the electrode 111 to the lead wire 101 from the driver circuit 20.

It is confirmed that the structure, disclosed herein to reduce the undesired parasitic resonance by restraining at least the vibrations at the center portion of the combined vibration mass M, is found effective to discriminate at least the unloaded condition from the loaded condition in terms of the electrically equivalent impedance of the vibration mass M over the frequency range of 1 MHz to 10 MHz. In this connection, the device of the present invention may be configured not to react with one of the abnormally loaded conditions shown in FIG. 2C, and therefore allow the use without the fluid F.

It is noted in this connection that the individual structures shown with reference to FIGS. 15, 16, 18 to 35 can be suitably combined for reducing the undesired parasitic resonance. Further, where the electrodes are concerned, it is possible that one of the electrodes can be given the above structure for reducing the vibrations at the center of the vibration mass, while leaving the other electrode to cover substantially entirely the corresponding face of the piezoelectric element 110.

The invention claimed is:

1. An ultrasound applying skin care device comprising:
a housing provided with an applicator head which applies ultrasound to a user's skin; and
a driver circuit which gives an electric pulse for actuating said applicator head to generate the ultrasound;
said applicator head comprising:
a vibrator element generating the ultrasound, and
a horn having a mounting face and a skin opposing face which is adapted in use to come into contact with the skin, said horn carrying said vibrator on said mounting face to transmit said ultrasound to the skin through said skin opposing face, said vibrator element and said horn being integrated into a combined vibration mass which resonates with the electric pulse of a resonant frequency from said driver circuit to generate the ultrasound, said combined vibration mass giving a first electrically equivalent impedance when it is normally loaded by contact with the skin, and gives a second electrically equivalent impedance when it is unloaded,
a load detecting circuit which is connected to monitor whether said combined vibration mass gives the first or second electrically equivalent impedance and provides a load detection signal only upon seeing said first electrically equivalent impedance,
a control circuit which limits or stops the electric pulse when the load detection signal is not received within a predetermined time period,
wherein said combined vibration mass has a structure that restrains vibrations at a center portion of said combined vibration mass to reduce a parasitic resonance, thereby differentiating said first electrically equivalent impedance from said second electrically equivalent impedance for discrimination therebetween, and
wherein said vibrator element comprises a piezoelectric element in the form of a circular disc having flat upper and lower end faces, and upper and lower electrodes respectively deposited on said upper and lower end faces, said electric pulse being applied across said upper and lower electrodes, and
wherein said horn has a center hole for restraining the vibrations at the center of said combined vibration mass.

2. The ultrasound applying skin care device as set forth in claim 1, wherein at least one of said upper electrode, said lower electrode, and said piezoelectric element has a center opening to restrain the vibrations at the center of said combined vibration mass.

3. The ultrasound applying skin care device as set forth in claim 2, wherein at least one of said upper electrode and said electrode has a diameter smaller than that of said piezoelectric element to leave the peripheral portions of the corresponding end face of said piezoelectric element uncovered.

4. The ultrasound applying skin care device as set forth in claim 1, wherein each of said upper electrode, said lower electrode, and said piezoelectric element has a center opening to restrain the vibrations at the center of said combined vibration mass.

5. The ultrasound applying skin care device as set forth in claim 1, wherein at least one of said upper and lower electrodes is divided by at least one slit into a plurality of identical segments, said at least one slit extending diametrically to leave the center and the diametrically extending band portion of said piezoelectric element uncovered.

6. The ultrasound applying skin care device as set forth in claim 1, wherein
at least one of said upper and lower electrodes has at least one slit that uncovers the center portion of said piezoelectric element.

7. The ultrasound applying skin care device as set forth in claim 1, wherein said upper electrode is covered on its center with an elastic member absorbing the vibrations at the center of said combined vibration mass.

8. The ultrasound applying skin care device as set forth in claim 7, wherein said elastic member is a silicone rubber.

9. The ultrasound applying skin care device as set forth in claim 1, wherein said upper electrode of said piezoelectric element is covered on its center with a solder bulk for electrical connection of the upper electrode to a lead wire leading from said driver circuit, the solder bulk adding a weight to the center of the piezoelectric element.

10. The ultrasound applying skin care device as set forth in claim 1, wherein
said horn is formed as an integral part thereof with a rim which surrounds said horn and is connected to said housing,
said horn and said rim defines therebetween a restrictor which restricts the ultrasound vibrations from propagating towards said rim.

11. The ultrasound applying skin care device as set forth in claim 10 wherein
said restrictor is defined by a cavity formed at the boundary between said horn and said rim.

12. The ultrasound applying skin care device as set forth in claim 1, further including:
a motion detecting circuit which monitors whether said combined vibration mass is moving and provides a motion detection signal when said vibration mass is so moving;
said control circuit controlling said driver circuit to stop or limit said electric pulse when said load detection signal is not received within said predetermined time period or when said motion detection signal is not continuous over a critical time duration even in the presence of said load detection signal being detected within said time period.

13. The ultrasound applying skin care device as set forth in claim 1, wherein
said control circuit receives said first electrically equivalent impedance in order to vary the intensity of the ultrasound generated at said vibrator element in accordance with the magnitude of said first electrically equivalent impedance.

* * * * *